US008044661B2

(12) United States Patent
Scholz (10) Patent No.: US 8,044,661 B2
(45) Date of Patent: Oct. 25, 2011

(54) METHOD FOR DETERMINING A THREE-DIMENSIONAL RECONSTRUCTION OF AN EXAMINATION OBJECT

(75) Inventor: Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 874 days.

(21) Appl. No.: 12/080,460

(22) Filed: Apr. 3, 2008

(65) Prior Publication Data

US 2008/0247624 A1   Oct. 9, 2008

(30) Foreign Application Priority Data

Apr. 4, 2007   (DE) .................... 10 2007 016 319

(51) Int. Cl.
*G01V 3/00* (2006.01)
(52) U.S. Cl. ......................... 324/300; 324/309
(58) Field of Classification Search .......... 324/300–322; 600/407–445; 345/626; 378/8; 382/154
See application file for complete search history.

(56) References Cited

U.S. PATENT DOCUMENTS

| 6,004,269 | A  | * | 12/1999 | Crowley et al. | 600/439 |
| 6,139,183 | A  | * | 10/2000 | Graumann | 378/206 |
| 6,206,566 | B1 | * | 3/2001 | Schuetz | 378/205 |
| 6,324,296 | B1 | * | 11/2001 | McSheery et al. | 382/107 |
| 6,379,041 | B1 | * | 4/2002 | Schuetz et al. | 378/205 |
| 6,634,088 | B1 | * | 10/2003 | Morrone | 29/607 |
| 6,845,142 | B2 | * | 1/2005 | Ohishi | 378/8 |
| 7,148,903 | B2 | * | 12/2006 | Brunner et al. | 345/626 |
| 7,280,686 | B2 | * | 10/2007 | Hornegger et al. | 382/154 |
| 7,555,157 | B2 | * | 6/2009 | Davidson et al. | 382/154 |
| 2008/0253522 | A1 | * | 10/2008 | Boyden et al. | 378/87 |

FOREIGN PATENT DOCUMENTS

| DE | 19526234 A1 | 1/1996 |
| DE | 10306016 A1 | 9/2004 |

OTHER PUBLICATIONS

Kalender, Willi A.; Hebel, Robert; Ebersberger, Johannes; "Reduction of CT artifacts caused by metallic implants"; Radiology; Aug. 1987; vol. 164, No. 2, pp. 576-577.

T. Hinderling, P. Rüegsegger, M. Anliker, C. Dietschi; Computed tomography reconstruction from hollow projections: an application to in vivo evaluation of artificial hip joints; Journal of Computer Assisted Tomography; Feb. 1979; vol. 3, No. 1; pp. 52-57.

(Continued)

*Primary Examiner* — Brij Shrivastav (57) ABSTRACT

A provisional three-dimensional reconstruction of an examination object is determined based on two-dimensional original projection images. Provisional metal volumes are determined on the reconstruction by segmentation and mapped into the original projection images to define provisional metal areas. Edge points on edge zones of the provisional metal areas are selected. Data values of the original projection images within the provisional metal areas are modified as a function of data values of the selected edge points to determine modified projection images. Differential images are determined based on the original projection images and the corresponding modified projection images. Definitive metal areas are determined in the differential images by segmentation. The differential images are added to the modified projection images with the definitive metal areas deducted. A definitive three-dimensional reconstruction of the examination object is determined based on the modified projection images including the added differential images.

12 Claims, 6 Drawing Sheets

OTHER PUBLICATIONS

D. Felsenberg, W. Kalender, R. Sokiranski, J. Ebersberger, R. Krämer; "Reduktion von Metallartefakten in der Computer Tomographie: Klinische Erfahrungen and Ergebnisse"; Electromedica, 1988; vol. 56, No. 3; pp. 97-104.

A.H. Mahnken, R. Raupach, J.E. Wildberger, B. Jung, N. Heussen, T.G. Flohr, R.W. Günther, S. Schaller; "A new algorithm for metal artifact reduction in computed tomography—in vitro and in vivo evaluation after total hip replacement"; Investigative Radiology; Dec. 2003; vol. 38, No. 12; pp. 769-775.

B. De Man, J. Nuyts, P. Dupont, G. Marchal, and P. Suetens; "Reduction of metal streak artifacts in x-ray computed tomography using a transmission maximum a posteriori algorithm"; IEEE Transactions on Nuclear Science, 2000, pp. 977-981; vol. 47, No. 3.

* cited by examiner

METHOD FOR DETERMINING A THREE-DIMENSIONAL RECONSTRUCTION OF AN EXAMINATION OBJECT

CROSS REFERENCE TO RELATED APPLICATIONS

This application claims priority of German application No. 10 2007 016 319.5 filed Apr. 4, 2007, which is incorporated by reference herein in its entirety.

FIELD OF THE INVENTION

The present invention relates to a determination method for determining a definitive three-dimensional reconstruction of an examination object on the basis of a plurality of two-dimensional original projection images.

BACKGROUND OF THE INVENTION

Metallic objects (for example catheters in vessels, platinum coils in aneurysms, dental fillings, protheses etc.) produce streak-like artifacts in X-ray computed tomography two-dimensional images, said artifacts extending across the entire image. If the artifacts are strong, the image is rendered diagnostically unusable as a result of the artifacts, since anatomical structures are covered. The same problem arises in the case of volume reconstructions from planar projection data, such as is acquired for example by means of C-arm systems and associated flat-panel detectors.

Various determination methods for determining a definitive three-dimensional reconstruction of an examination object with the aid of a plurality of two-dimensional original projection images are known from U.S. Pat. No. 7,148,903 B2. A reduction in metallic artifacts is possible using the determination methods described therein. With the known methods—irrespective of whether a provisional three-dimensional reconstruction of the examination object is determined within the scope of the determination methods or not—metal areas are determined directly in the original projection images, which metal areas are produced by metallic objects in the beam path. Data values of the original projection images which are assigned to locations that lie in the metal areas are modified. In this way modified projection images are determined. The images can be modified as a function of data values which are assigned to edge zones of the metal areas. Finally, the definitive three-dimensional reconstruction of the examination object is determined based on the modified projection images.

The approaches described in U.S. Pat. No. 7,148,903 B2 enable a substantial reduction in metal artifacts in a multiplicity of application situations. However, in many application situations—in particular when areas filled with contrast agent are present in the original projection images—it is difficult to impossible to differentiate metal and contrast agent using the approaches of U.S. Pat. No. 7,148,903 B2. It is also difficult, using the known determination methods, to detect small metal objects in the original projection images.

Iterative reconstruction methods are also known. With these reconstruction methods, streak artifacts can be reduced by including the data acquisition and the data statistics in the reconstruction algorithm. Iterative reconstruction methods are very compute-intensive, however.

SUMMARY OF THE INVENTION

The object of the present invention consists in providing a determination method of the kind referred to in the introduction and the equipment-related objects corresponding herewith, by means of which the metal areas can be reliably determined even in unfavorable constellations (small metal objects and/or areas filled with contrast agent).

The object is achieved by the claims.

According to the invention a provisional three-dimensional reconstruction of the examination object is determined on the basis of the original projection images. In the provisional three-dimensional reconstruction, provisional metal volumes are determined by means of segmentation. Corresponding provisional metal areas are determined by mapping the provisional metal volumes into the original projection images. Edge zones of the provisional metal areas are determined in the original projection images. Edge points of the edge zones are selected. Data values of the original projection images which are assigned to locations that lie in the provisional metal areas are modified as a function of data values which are assigned to the selected edge points. In this way modified projection images are determined. A differential image is determined in each case on the basis of the respective original projection image and the corresponding modified projection image. Definitive metal areas are determined in the differential images by means of segmentation. The differential images, with the respective definitive metal areas subtracted, are added to the corresponding modified projection image in each case. The definitive three-dimensional reconstruction of the examination object is determined on the basis of the modified projection images including the added differential images.

It is possible, for the purpose of determining the modified data values, to make use of the data values of the edge zones as they are. Preferably, however, the data values of the edge zones are filtered in order to reduce noise effects.

It is possible, for the purpose of determining the modified data values, to make use of the data values of all of the edge zones. Preferably, however, the selected edge points include only a part of the edge zones. By means of this measure the computing overhead for determining the modified data values can be significantly reduced. In contrast, the modified data values are changed only to an insignificant extent.

It is possible to determine the modified data values uniformly for all locations that lie in the provisional metal areas. Preferably, however, the modified data values are determined as a function of the location in the provisional metal area which is assigned to the data value that is to be modified. In particular it is possible for the modified data values to be determined on the basis of the data values of the selected edge points and the distances of the location assigned to the respective data value that is to be modified in the provisional metal area from the selected edge points.

As a rule it is sufficient for only the data values of the edge zone of the respective original projection image to be included in the determination of the modified data values. In some cases, however, it leads to better results if edge points of provisional metal areas in locally adjacent original projection images are also included in the determination of the modified data values.

Generally, at least one two-dimensional representation of the definitive three-dimensional reconstruction of the examination object is determined. The two-dimensional representation can be, for example, a perspective projection, a parallel projection or a representation of a layer of the three-dimensional reconstruction. It can be of advantage if definitive metal volumes are determined on the basis of the definitive metal areas and the definitive metal volumes are inserted into the two-dimensional representation of the definitive three-dimensional reconstruction.

The modified projection images can be used directly for determining the definitive three-dimensional reconstruction of the examination object. However, it generally leads to better results if the modified projection images, including the added differential images, are preprocessed by means of an image preprocessing method that acts two-dimensionally and the definitive three-dimensional reconstruction of the examination object is determined on the basis of the preprocessed projection images. For example, a gradient determination with subsequent smoothing can be performed.

BRIEF DESCRIPTION OF THE DRAWINGS

Further advantages and details will emerge from the following description of exemplary embodiments in conjunction with the drawings, in which are shown in schematic representation.

DETAILED DESCRIPTION OF THE INVENTION

Figure 1:
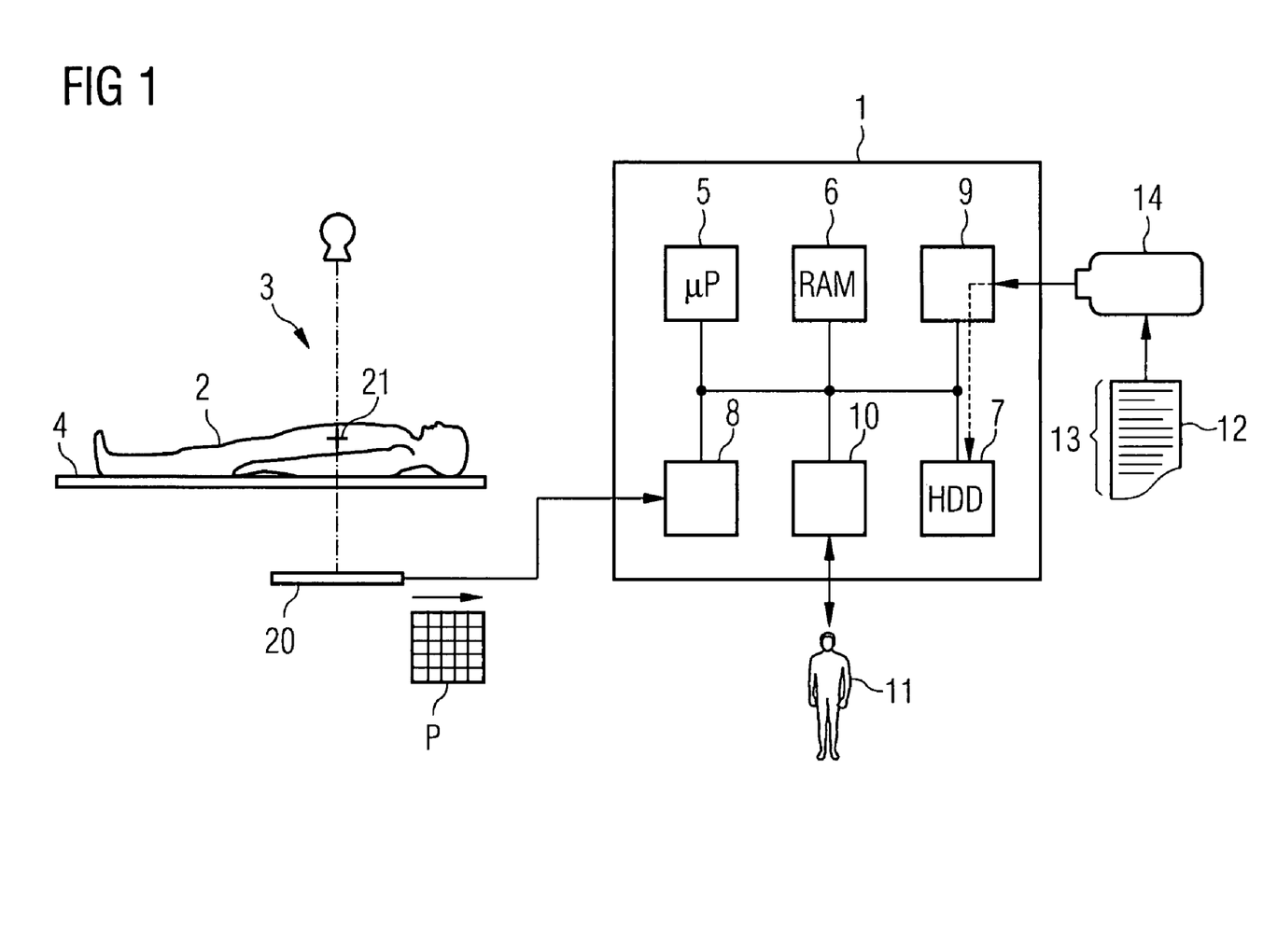
FIG. 1 a block diagram of a data acquisition and processing device.

According to FIG. 1, a computer 1 is supplied with a plurality (for example 40 to 400) two-dimensional projection images P of an examination object 2. The examination object 2 is normally a human being. The projection images P are typically fluoroscopic images that are acquired by means of an X-ray system 3. For the purpose of acquiring the projection images P, the examination object 2 can be disposed for example on a patient examination table 4.

A three-dimensional reconstruction of the examination object 2 is to be determined by the computer 1 using the projection images P. Determination methods of this kind are generally known as such to persons skilled in the art. The preconditions which must be fulfilled by the projection images P so that the determination of the three-dimensional reconstruction will be possible are also known to persons skilled in the art. The basic principle for determining a three-dimensional reconstruction on the basis of a plurality of projection images P will therefore not be dealt with in greater detail below.

The computer 1 is embodied in typical fashion. It includes a microprocessor 5, a working memory (RAM) 6, a mass storage device 7 (e.g. a hard disk), a projection interface 8 to the X-ray system 3, a data interface 9 (e.g. a USB port) and a user interface 10 (e.g. keyboard, mouse and display).

The computer 1 communicates with a user 11 via the user interface 10. By way of the data interface 9 the computer 1 can receive a computer program 12 and store it in the mass storage device 7. The computer program 12 has machine code 13 which can be executed by the computer 1 (that is to say by the microprocessor 5 of the computer 1). The computer program 12 is stored on a data medium 14 (e.g. a USB memory stick) and can be supplied to the computer 1 in this way. When appropriate invocation commands are issued to the computer 1 by the user 11, the computer 1 loads the computer program 12 from the mass storage device 7 into the working memory 6 and executes it. The execution of the computer program 12 causes the computer 1 to carry out a determination method for the purpose of determining a definitive three-dimensional reconstruction of the examination object 2. The determination method is explained in more detail below with reference to FIGS. 2 to 4.

Figures 2, 2A:
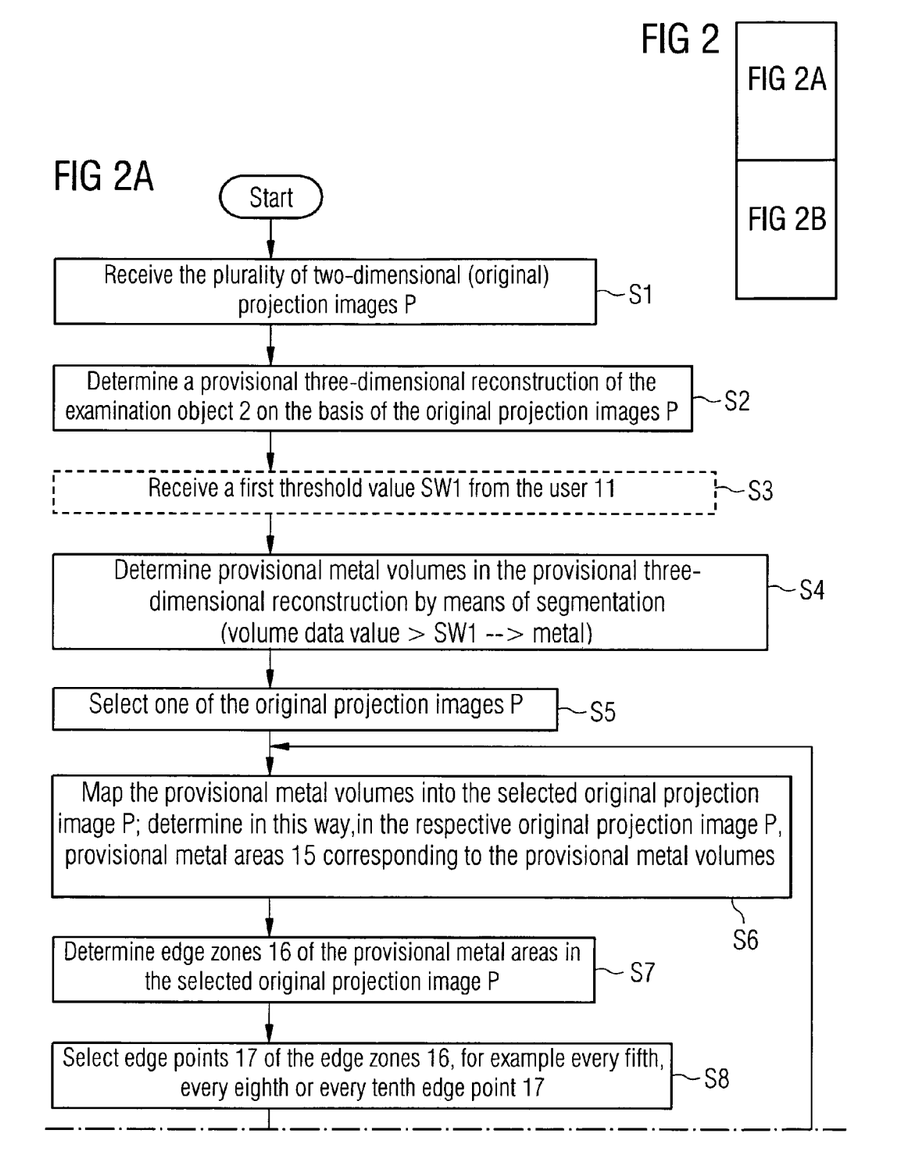
FIG. 2 a flowchart.
Figure 2B:
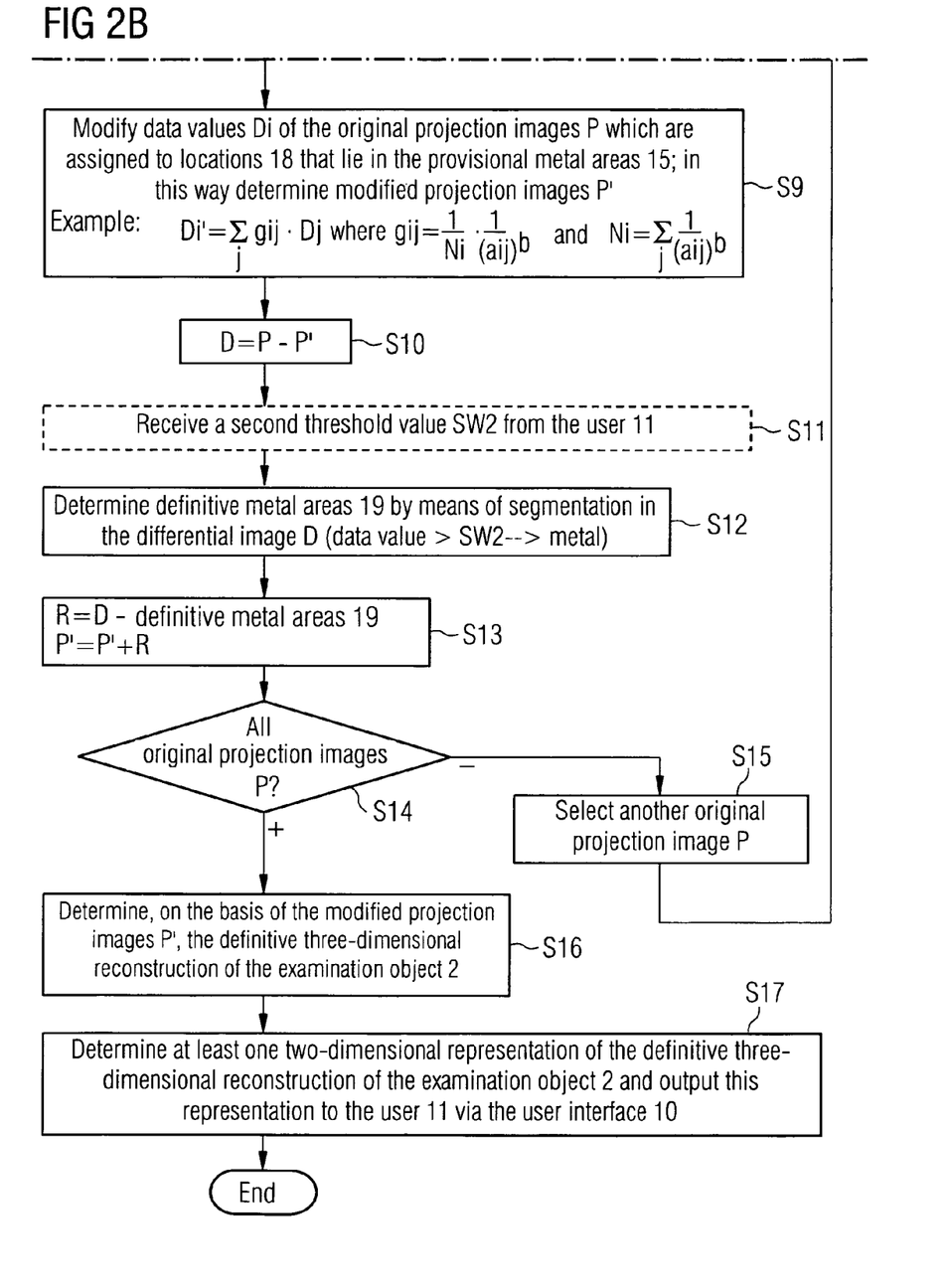

According to FIG. 2, the computer 1 initially receives the plurality of two-dimensional projection images P in a step S1. The received projection images P are referred to in the following as original projection images P.

In a step S2, the computer 1 determines a provisional three-dimensional reconstruction of the examination object 2 on the basis of the original projection images P. As already mentioned, the corresponding determination methods are known as such to persons skilled in the art. The so-called Feldkamp algorithm may be mentioned purely by way of example.

In a step S3, the computer 1 receives a first threshold value SW1 from the user 11. Step S3 is merely optional and is therefore represented by a dashed line in FIG. 2. If it is omitted, either the first threshold value SW1 is predefined as a fixed value or the first threshold value SW1 is determined automatically by the computer 1. An automatic determination can be performed for example on the basis of the data values of the provisional reconstruction.

In a step S4, the computer 1 determines provisional metal volumes in the provisional three-dimensional reconstruction by means of segmentation. In the course of step S4, the computer 1 in particular compares the volume data values of the provisional three-dimensional reconstruction individually with the first threshold value SW1. If the volume data values are greater than the first threshold value SW1, the computer 1 classifies the corresponding volume element as metal, and otherwise as non-metal.

In a step S5, the computer 1 selects a first of the original projection images P. In a step S6, the computer 1 maps the provisional metal volumes into the currently selected original projection image P. In this way it determines, in the respective original projection image P, provisional metal areas 15 that correspond to the provisional metal volumes (see FIG. 3).

Figure 3:
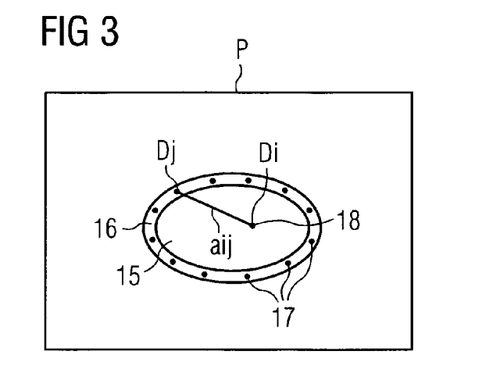
FIG. 3 a two-dimensional projection image.

In a step S7, the computer 1 determines edge zones 16 of the provisional metal areas 15 in the selected original projection image P. For example, the computer 1 can assign a data value "1" to the provisional metal areas 15, and a data value "0" to the remaining areas. In this case the edge zones 16 can be determined for example by means of a simple edge detection which is generally known to persons skilled in the art. It should be pointed out here as a matter of form that the term "edge zones" is meant to denote those areas of the original projection image P which border on the provisional metal areas 15, but still lie outside the provisional metal areas 15.

In a step S8, the computer 1 selects edge points 17 of the edge zones 16. In the simplest case the computer 1 selects at this juncture all points 17 that lie in the edge zones 16, though preferably (compare FIG. 3) the computer selects only a part of the edge zones 16, for example every fifth, every eighth or every tenth edge point 17. Usually the edge points 17 are selected in such a way that they are distributed (at least essentially) evenly over the edge zones 16.

In a step S9, the computer 1 modifies data values Di of the original projection images P which are assigned to locations 18 that lie in the provisional metal areas 15. In this case the data values Di are modified preferably as a function of data values Dj which are assigned to the selected edge points 17. In this way the computer determines modified projection images P'.

In the simplest case the computer 1 determines a single data value in the course of step S9 and replaces all data values Di which are assigned to locations 18 within the metal areas 15 by this one modified data value. Preferably, however, the computer 1 determines the modified data values Di' as a function of the location 18 in the provisional metal area 15 which is assigned to the data value Di that is to be modified. In particular, the computer 1—see FIG. 3—can weight the data values Dj of the selected edge points 17 with weighting factors gij, which depend on the distances aij of the respective selected edge points 17 from the respective location 18. In this case the computer 1 determines the modified data values Di' on the basis of the data values Dj of the selected edge points 17 and the distances aij of the location 18 assigned to the respective data value Di that is to be modified in the provisional metal area 15 from the selected edge points 17.

The weighting factors gij are intended to ensure in particular that selected edge points 17 which lie closer to the respective location 18 than other edge points 17 are weighted more heavily. For example, the weighting factor gij of the jth edge point 17 can be determined for calculating the modified data value Di' of the ith location 18 in the metal area 15 as $$gij = \frac{1}{Ni} \cdot \frac{1}{(aij)^b} \quad (1)$$

In this case aij is the distance of the ith location 18 in the metal area 15 from the jth edge point 17, b is a suitably chosen exponent, and Ni is a normalization factor. It is defined as $$Ni = \sum_j \frac{1}{(aij)^b} \quad (2)$$

so that consequently $$\sum_j gij = 1 \quad (3)$$

applies.

In a step S10, the computer 1 determines a differential image D on the basis of the respective original projection image P and the corresponding modified projection image P'.

In a step S11, the computer 1 receives a second threshold value SW2 from the user 11. Analogously to step S3, step S11 is also merely optional and is therefore represented by a dashed line in FIG. 2. If step S11 is omitted, the second threshold value SW2 (analogously to the first threshold value SW1) can be specified as a fixed value. Alternatively it is possible for the second threshold value SW 2 to be determined automatically by the computer 1, for example on the basis of the data values of the respective differential image D.

Figure 4:
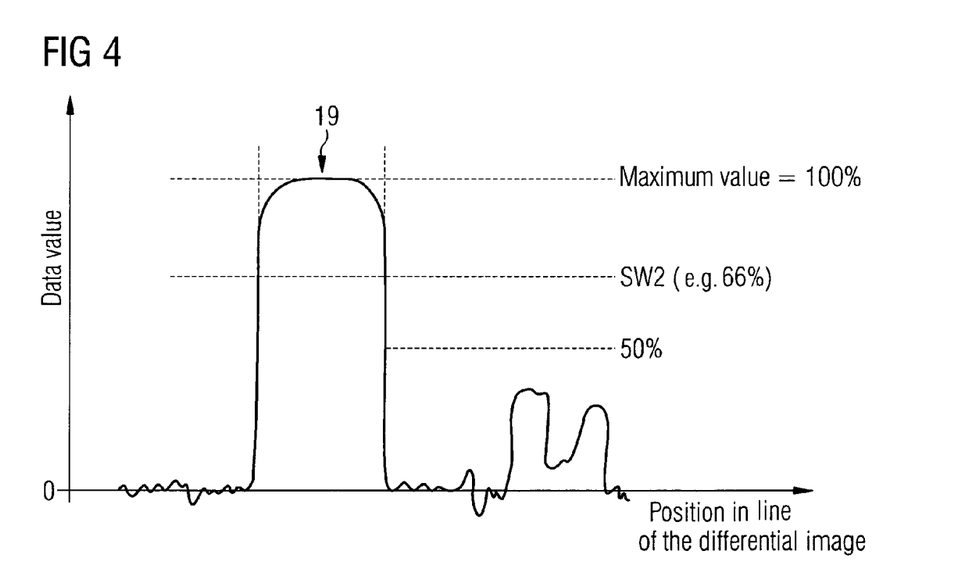
FIG. 4 a line in a projection image.

In a step S12, the computer 1 determines definitive metal areas 19 by means of segmentation in the differential image D (compare FIG. 4). In particular, the computer 1 can compare the data values with the second threshold value SW 2 in the differential images D. If the respective data value exceeds the second threshold value SW2, the corresponding location is assigned to a definitive metal area 19; otherwise it is classified as non-metal.

Step S12 is based on the knowledge that in the ideal case the differential images D only contain metal. It is, however, possible that they also include other constituents besides metal. Generally, however, the data values that are attributable to metal are considerably greater than the data values that are not attributable to metal. In particular, the data values that are not attributable to metal are, according to FIG. 4, typically maximally around half as large as the data values that are attributable to metal. Therefore the definitive metal areas 19 can be separated from the remaining areas in the differential image D by suitable selection of the second threshold values SW2.

In a step S13, the computer 1 determines a residual image R. The computer 1 adds the residual image R to the modified projection image P' in step S13. The residual image R corresponds to the differential image D with the definitive metal areas 19 of the respective differential image D deducted.

In a step S14, the computer 1 checks whether it has already performed steps S6 to S13 for all the original projection images P. If this is not the case, the computer 1 proceeds to a step S15. In step S15, the computer 1 selects another, hitherto not yet selected original projection image P. It then returns to step S6.

When the computer 1 has performed steps S6 to S13 for all the original projection images P, it proceeds to a step S16. In step S16, the computer 1 determines on the basis of the modified projection images P' (including the added differential images D) the definitive three-dimensional reconstruction of the examination object 2.

Finally, the computer 1 performs a step S17. In step S17, the computer 1 determines at least one two-dimensional representation of the definitive three-dimensional reconstruction of the examination object 2 and outputs this representation to the user 11 via the user interface 10.

The inventive determination method explained in detail above can be modified in various ways. This is explained in more detail below with reference to FIGS. 5 to 7. The modifications of FIGS. 5 to 7 can in this case be realized independently of one another. They can therefore be realized individually, in pairs and collectively.

Figure 5:
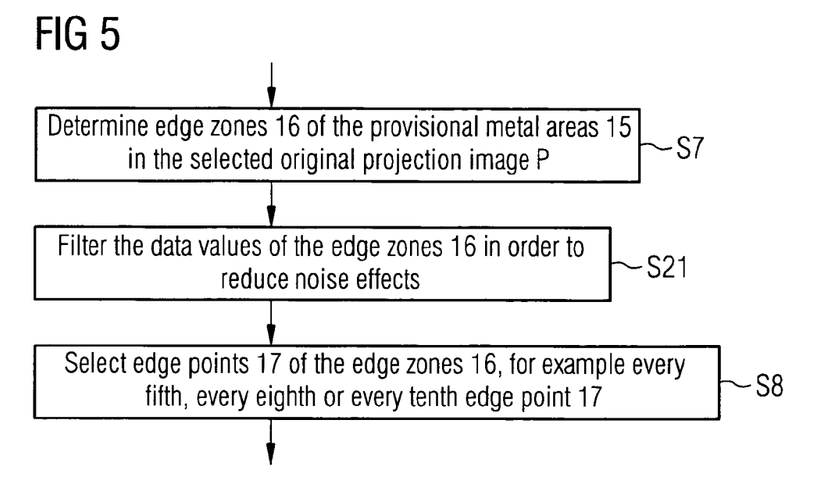
FIG. 5 a flowchart.

According to FIG. 5, a step S21 is inserted between steps S7 and S8. In step S21, the computer 1 filters the data values of the edge zones 16. The filtering is intended to reduce noise effects.

Inserting step S21 is beneficial in particular when the selected edge points 17 comprise only a part of the edge zones 16. This is also represented thus in FIG. 5. In principle, however, the insertion of step S21 can be implemented independently of whether the selected edge points 17 comprise all of the edge zones 16 or only a part of the edge zones 16.

Figure 6:
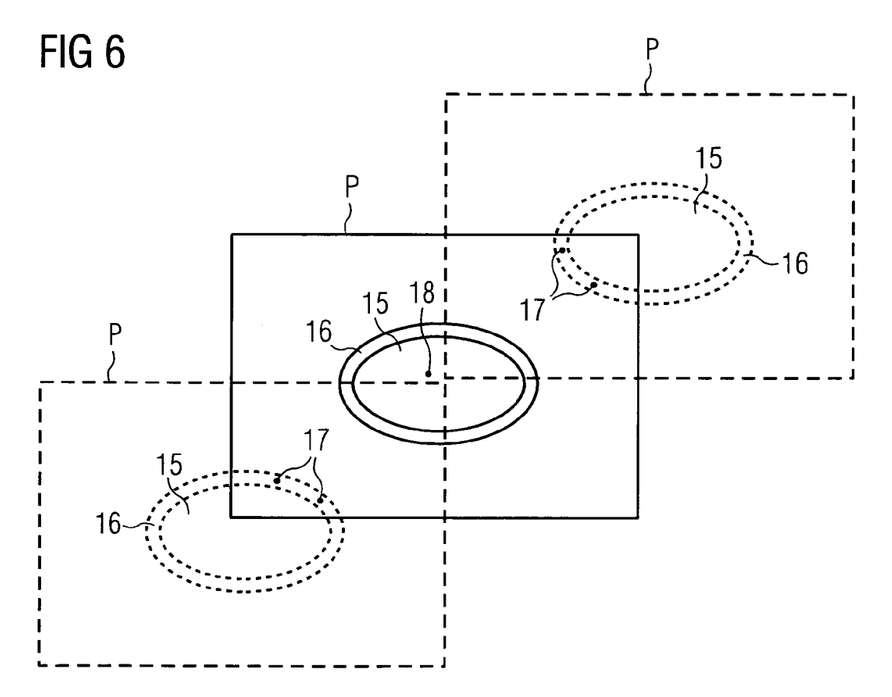
FIG. 6 several two-dimensional projection images.

According to FIG. 6, it is possible in the course of step S9 also to include edge points 17 of provisional metal areas 15 in locally adjacent original projection images P in the determination of the modified data values Di'. The corresponding calculation of the distance between two points which are assigned to different original projection images P results in this case in $$d12 = \sqrt{(\rho 12)^2 + (v2-v1)^2} \quad (4)$$

where the relation $$(\rho 12)^2 = R1^2 + R2^2 + u1^2 + u2^2 - 2(R1 \cdot R2 + u1 \cdot u2) \cdot \cos(\alpha 2 - \alpha 1) - \quad (5)$$
$$2(R1 \cdot u2 - R2 \cdot u1) \cdot \sin(\alpha 2 - \alpha 1)$$

applies. The supplements 1 and 2 in the variables R1, R2 etc. serve here to distinguish two detector points 1 and 2 which belong to different original projections P1, P2, the original projections P1, P2 having been captured at angles α1 and α2. u designates the column coordinates of the original projection images P1, P2 in length units, v the row coordinates in length units. R is the distance of the detector 20 from a center of rotation 21.

Figure 7:
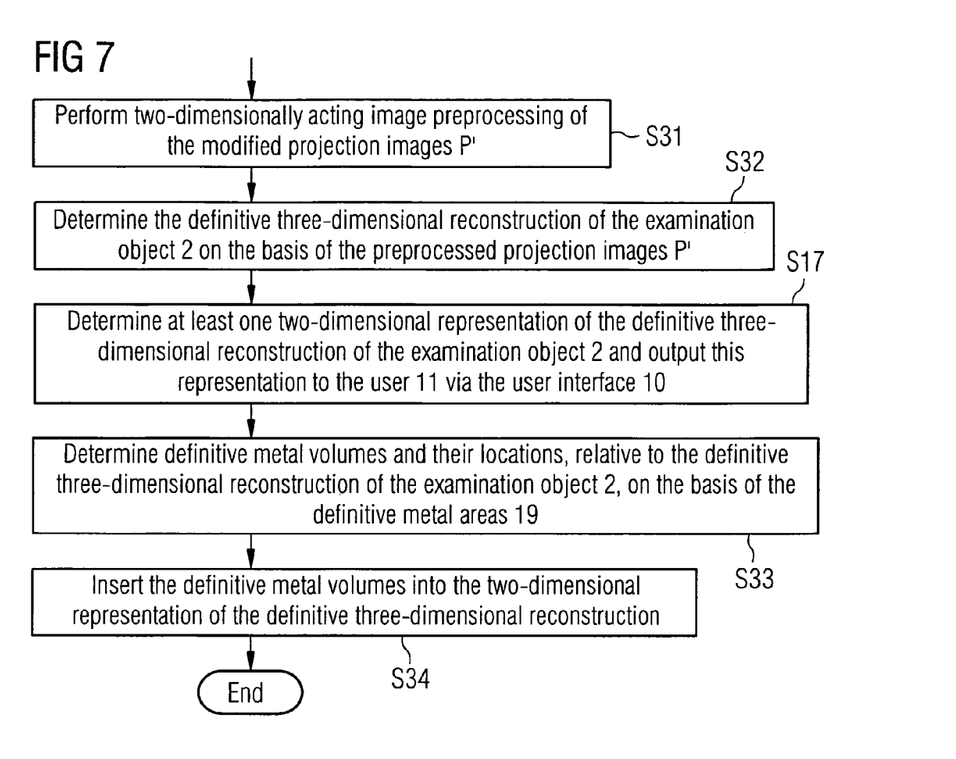
FIG. 7 a flowchart.

Finally, it is possible to modify or supplement steps S16 and S17 according to FIG. 7. Step S16 from FIG. 2 is in this case modified in FIG. 7 by steps S31 and S32, and step S17 is supplemented by steps S33 and S34. The two measures of FIG. 7 (that is to say steps S31 and S32 on the one hand and steps S33 and S34 on the other) can in this case be realized independently of one another. They can therefore be realized individually or in combination.

Figure 8:
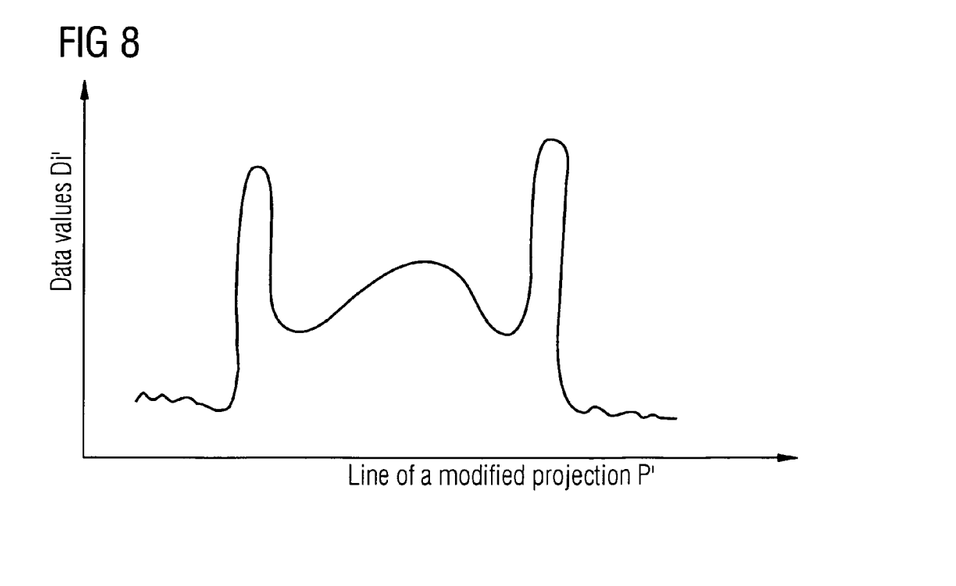
FIG. 8 a line in a modified projection image.

In step S31, the computer 1 performs image preprocessing of the modified projection images P' that acts in a two-dimensional manner. In this case the residual images R have already been added to the modified projection images P'. For example, the computer 1—compare FIG. 8—can perform a gradient detection together with subsequent smoothing of large gradients. In step S32, the computer 1 determines the definitive three-dimensional reconstruction of the examination object 2 on the basis of the preprocessed projection images P'.

In step S33, the computer 1 determines definitive metal volumes and their locations, relative to the definitive three-dimensional reconstruction of the examination object 2, on the basis of the definitive metal areas 19. In step S34, the computer 1 inserts the definitive metal volumes into the two-dimensional representation of the definitive three-dimensional reconstruction.

The determination methods according to the invention have many advantages. In particular they are easy to implement, and operate robustly, reliably and accurately. Furthermore they also lead to good results in cases where determination methods of the prior art fall short (in spite of artifact reduction there).

The above description serves solely to explain the present invention. The scope of protection of the present invention, on the other hand, is to be defined solely by the attached claims.

The invention claimed is:

1. A method for determining a three-dimensional reconstruction of an examination object, comprising:
    determining a provisional three-dimensional reconstruction of the examination object based on a plurality of two-dimensional original projection images of the examination object;
    segmenting the provisional three-dimensional reconstruction to determined a provisional metal volume;
    mapping the provisional metal volume into the original projection images to create a plurality of corresponding provisional metal areas;
    defining edge zones of the provisional metal areas in the original projection images;
    selecting edge points from the edge zones;
    determining modified projection images by modifying data values of the original projection images assigned to locations in the provisional metal areas as a function of data values of the selected edge points;
    calculating differential images based on the original projection images and the corresponding modified projection images;
    segmenting the differential images to determine definitive metal areas;
    subtracting the definitive metal areas from the differential images; and
    determining the three-dimensional reconstruction by adding the subtracted differential images to the corresponding modified projection images.

2. The method as claimed in claim 1, wherein data values of the edge zones are filtered to reduce noise effects.

3. The method as claimed in claim 1, wherein the selected edge points comprise a part of the edge zones.

4. The method as claimed in claim 1, wherein the data values of the original projection images are uniformly modified to the locations in the provisional metal areas.

5. The method as claimed in claim 1, wherein the data values of the original projection images are modified to the locations in the provisional metal areas that are assigned to the data values to be modified.

6. The method as claimed in claim 5, wherein the data values of the original projection images are modified based on the data values of the selected edge points and distances between the locations in the provisional metal area and the selected edge points.

7. The method as claimed in claim 1, wherein the selected edge points comprise edge points of the provisional metal areas in locally adjacent original projection images.

8. The method as claimed in claim 1, wherein a definitive metal volume is determined based on the definitive metal areas and inserted into a two-dimensional representation of the three-dimensional reconstruction.

9. The method as claimed in claim 1, wherein the modified projection images are preprocessed after adding the subtracted differential images.

10. The method as claimed in claim 9, wherein the three-dimensional reconstruction is determined based on the preprocessed modified projection images.

11. A non-transitory computer program executed on a computer for determining a three-dimensional reconstruction of an examination object, comprising:
    a subroutine that:
        determines a provisional three-dimensional reconstruction of the examination object based on a plurality of two-dimensional original projection images of the examination object;
        segments the provisional three-dimensional reconstruction to determined a provisional metal volume;
        maps the provisional metal volume into the original projection images to create a plurality of corresponding provisional metal areas;
        defines edge zones of the provisional metal areas in the original projection images;
        selects edge points from the edge zones;
        determines modified projection images by modifying data values of the original projection images assigned to locations in the provisional metal areas as a function of data values of the selected edge points;
        calculates differential images based on the original projection images and the corresponding modified projection images;
        segments the differential images to determine definitive metal areas;
        subtracts the definitive metal areas from the differential images; and
        determines the three-dimensional reconstruction by adding the subtracted differential images to the corresponding modified projection images.

12. A medical device for determining a three-dimensional reconstruction of an examination object, comprising:
    an image device that records a plurality of two-dimensional original projection images of the examination object; and a computer that:
  determines a provisional three-dimensional reconstruction of the examination object based on the two-dimensional original projection images;
  segments the provisional three-dimensional reconstruction to determined a provisional metal volume;
  maps the provisional metal volume into the original projection images to create a plurality of corresponding provisional metal areas;
  defines edge zones of the provisional metal areas in the original projection images;
  selects edge points from the edge zones;
  determines modified projection images by modifying data values of the original projection images assigned to locations in the provisional metal areas as a function of data values of the selected edge points;
  calculates differential images based on the original projection images and the corresponding modified projection images;
  segments the differential images to determine definitive metal areas;
  subtracts the definitive metal areas from the differential images; and
  determines the three-dimensional reconstruction by adding the subtracted differential images to the corresponding modified projection.

* * * * *